United States Patent
Lee et al.

(10) Patent No.: US 9,535,036 B2
(45) Date of Patent: Jan. 3, 2017

(54) MULTIPLE DISCRIMINATION DEVICE AND METHOD OF MANUFACTURING THE DEVICE

(71) Applicant: Electronics and Telecommunications Research Institute, Daejeon (KR)

(72) Inventors: Dae-Sik Lee, Daejeon (KR); Jeong Won Park, Daejeon (KR); Seong-Mok Cho, Daejeon (KR); Moon Youn Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 129 days.

(21) Appl. No.: 14/029,677

(22) Filed: Sep. 17, 2013

(65) Prior Publication Data

US 2014/0017773 A1 Jan. 16, 2014

Related U.S. Application Data

(63) Continuation-in-part of application No. 13/527,330, filed on Jun. 19, 2012, now abandoned.

(30) Foreign Application Priority Data

Nov. 26, 2012 (KR) .......................... 10-2012-0134667
Aug. 12, 2013 (KR) .......................... 10-2013-0095485

(51) Int. Cl.
*B01D 21/00* (2006.01)
*G01N 27/74* (2006.01)
(Continued)

(52) U.S. Cl.
CPC ............. *G01N 27/745* (2013.01); *B29C 65/70* (2013.01); *B29C 65/72* (2013.01);
(Continued)

(58) Field of Classification Search
CPC ................ B01L 2200/0636; B01L 2200/0647; B01L 2200/0668; B01L 2300/0864; B01L 2400/043; B01L 3/502761; B01L 3/502776; B01L 2200/0652; B01L 2300/0867; B01L 7/52; B03C 1/288; B03C 1/32; B03C 2201/18; C12M 27/16; C12M 47/02; C12N 1/02; C12Q 2563/143; C12Q 2565/629; G01N 33/54326; G01N 27/745; G01R 33/0385; G01R 33/1269; B29C 65/72; B29C 65/70; B82Y 5/00; H01F 1/0054
See application file for complete search history.

(56) References Cited

U.S. PATENT DOCUMENTS 4,910,148 A 3/1990 Sorensen et al.
7,807,454 B2 10/2010 Oh et al.
(Continued)

FOREIGN PATENT DOCUMENTS

KR WO 2012033291 A2 * 3/2012 ........... B03C 1/0335

OTHER PUBLICATIONS

Sunitha Nagrath et al., "Isolation of rare circulating tumour cells in cancer patients by microchip technology", Nature, Dec. 2007, pp. 1235-1239, vol. 450, No. 20.

*Primary Examiner* — Dennis M White (57) ABSTRACT

Provided are a multiple discrimination device and a method of manufacturing the same. According to the multiple discrimination device, a three-dimensional micro ferromagnetic pattern is optimally designed and arranged to allow a magnetic force applied to a discrimination-target particle to be discriminated to be well controlled to perform discrimination well. The method employs a semiconductor processing technology, thereby precisely manufacturing and allowing mass production.

16 Claims, 9 Drawing Sheets

(51) Int. Cl.
  *B29C 65/70* (2006.01)
  *B29C 65/72* (2006.01)
  *G01R 33/12* (2006.01)
  *G01R 33/038* (2006.01)
  *B82Y 5/00* (2011.01)
  *H01F 1/00* (2006.01)

(52) U.S. Cl.
  CPC ..... *G01R 33/0385* (2013.01); *G01R 33/1269* (2013.01); *B82Y 5/00* (2013.01); *H01F 1/0054* (2013.01)

(56) References Cited

U.S. PATENT DOCUMENTS

| | | | |
|---|---|---|---|
| 2005/0284817 A1* | 12/2005 | Fernandez | B01F 13/0059 |
| | | | 210/695 |
| 2008/0124779 A1* | 5/2008 | Oh et al. | 435/173.9 |
| 2013/0017538 A1* | 1/2013 | Ionescu-Zanetti | B03C 1/288 |
| | | | 435/6.11 |
| 2013/0189755 A1* | 7/2013 | Han | B03C 1/0335 |
| | | | 435/173.9 |

* cited by examiner

MULTIPLE DISCRIMINATION DEVICE AND METHOD OF MANUFACTURING THE DEVICE

CROSS-REFERENCE TO RELATED APPLICATIONS

This U.S. non-provisional patent application claims priority under 35 U.S.C. §119 of Korean Patent Application No. 10-2012-0134667, filed on Nov. 26, 2012, and Korean Patent Application No. 10-2013-0095485, filed on Aug. 12, 2013, the entire contents of which are hereby incorporated by reference.

This application is a continuation-in-part of U.S. patent application Ser. No. 13/527,330, filed Jun. 19, 2012, entitled "MULTIPLE SEPARATION DEVICE AND METHOD FOR SEPARATING CANCER CELLS IN BLOOD USING THE DEVICE."

BACKGROUND OF THE INVENTION

The present invention disclosed herein relates to a multiple discrimination device for species of material including biomass and a method of manufacturing the device.

In the medical field, it is necessary to discriminate a cellular type or an intracellular constituent as a preparative tool for a final target or different analysis in diagnosis, treatment, and research fields. For example, it is needed to analyze a cancer cell. Blood cancer cells commonly designate cancer cells existing in peripheral blood of a cancer patient, which are cancer cells separated from a primary lesion or a metastatic lesion. Such blood cancer cells are expected as an influential biomarker for cancer diagnosis, prognostic analysis, and micrometastatic analysis. In addition, compared to typical cancer diagnosis methods, since using a non-invasive method, blood cancer cell analysis is very a promising future cancer diagnosis method. However, since a proportion of blood cancer cells in blood is one cancer cell per one billion of the entire cells or one cancer cell per $10^6$ to $10^7$ of white blood cells, which is very low, it is difficult to precisely analyze and a very exquisite analysis method is necessary.

Although various methods have been researched as a method of discriminating cancer cells from blood, much time is necessary to check, only information on existence and an amount of cancer cells and is provided, and it is difficult to analyze a type of cancer. Also, an interference caused by a specific-coupled blood cells occurs.

SUMMARY OF THE INVENTION

The present invention provides a multiply discrimination device for species of material including biomass and a method of manufacturing the device.

Embodiments of the present invention provide multiple discrimination devices including: a channel in which a mixture solution flows in a first direction and at least one ferromagnetic pattern disposed below a bottom of the channel. A slope of a tangent of the ferromagnetic pattern continuously varies with a location of the channel, and the mixture solution includes a discrimination-target particle and a nontarget particle.

In some embodiments, an angle between a tangent and the first direction at a part of the ferromagnetic pattern may be from about 80 to about 90 degrees.

In other embodiments, the ferromagnetic pattern may have at least one of shapes of 'J', 'U', and 'ω'.

In still embodiments, a linear width of the ferromagnetic pattern may vary with a location.

In even embodiments, a width of the ferromagnetic pattern may be from about 10 μm to about 1000 μm.

In yet embodiments, a thickness of the ferromagnetic pattern may be from about 0.1 μm to about 1000 μm.

In further embodiments, a height of the channel may be from about 10 μm to about 1000 μm.

In still further embodiments, the device may further include at least one permanent magnet disposed adjacently to the channel.

In even further embodiments, the device may further include at least one mixture solution inlet connected to the channel, to which the mixture solution is injected, a buffer solution inlet connected to the channel, a target particle outlet connected to the channel, through which the discrimination-target particle is discharged, and a nontarget particle outlet connected to the channel, through which the nontarget particle is discharged. The mixture solution inlet and the nontarget particle outlet may be connected to one side of the channel, and the buffer solution inlet and the target particle outlet may be connected to another side of the channel, separated from the one side.

In yet further embodiments, the number of ferromagnetic may be plural, and an interval between the ferromagnetic patterns may become narrower as closer to the nontarget particle outlet.

In much further embodiments, an angle between the another side of the channel and a tangent of the ferromagnetic pattern at the another side is from about 80 to about 90 degrees.

In still much further embodiments, a magnetization amount of the discrimination-target particle may be larger than that of the nontarget particle.

In even much further embodiments, the discrimination-target particle may be coupled with a magnetic nano particle and is at least one of a gene, DNA, RNA, protein, peptide, and a tumor cell.

In yet much further embodiments, the device may further include a bottom plate on which the ferromagnetic pattern is disposed and a top plate disposed above the bottom plate and including an inner space for providing the channel. At least one of the bottom plate and the top plate may include polydimethylsiloxane (PDMS).

In further embodiments, the device may further include a photoresist pattern disposed between the bottom plate and the top plate and being in contact with a sidewall of the ferromagnetic pattern.

In other embodiments of the present invention, methods of manufacturing a multiple discrimination device include forming a bottom plate including photoresist patterns on a top surface thereof and a ferromagnetic pattern between the photoresist patterns, forming a top plate including a recessed part therein and a plurality of holes connected to the recessed part, and coupling the bottom plate with the top plate.

In other embodiments, the coupling of the bottom plate and the top plate may include bonding the top plate to the bottom plate by using an adhesive.

In still other embodiments, the forming of the bottom plate may include forming a seed layer on a top of the bottom plate, forming the photoresist patterns on the seed layer, and forming the ferromagnetic pattern between the photoresist patterns by performing a plating process.

In even other embodiments, the forming of the top plate may include preparing a sacrificial substrate, forming a sacrificial photoresist pattern on the sacrificial substrate, forming a mold film covering the sacrificial photoresist pattern, on the sacrificial substrate, forming a recessed part in the mold film by removing the sacrificial substrate and the sacrificial photoresist pattern, and making holes in the mold film to be connected to the recessed part.

In yet other embodiments, the mold film may include PDMS.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIGS. 6A to 6D are views illustrating a method of manufacturing a top plate of FIG. 1B.

DETAILED DESCRIPTION OF PREFERRED EMBODIMENTS

Hereinafter, the embodiments of the present invention will be described in detail with reference to the attached drawings. However, the present invention is not limited to the disclosed embodiments but may be embodied in various shapes and may be diversely changed. However, the embodiments are described to perfectly disclose the present invention and provided to allow a person skilled in the art to fully understand the scope of the present invention. In the attached drawings, sizes of elements are enlarged rather than real sizes thereof for convenience of description and ratios of respective elements may be exaggerated or reduced.

When it is mentioned that an element is "on" or "connected to" another element, the element may be in direct contact with or connected to the other element but may be understood as still another element may exist therebetween. On the other hand, when it is mentioned that an element is "directly on" or "directly connected to" another element, it may be understood that there is no other elements therebetween. Other expressions describing relation between elements, for example, "between" or "direct between" may be understood in like manner.

Terms such as a first and a second may be used to describe various elements, but the elements are not limited to the terms. The terms are used only to distinguish one element from another element. For example, within the scope of the present invention, a first element may be designated as a second element, and similarly, the second element may be designated as the first element.

Singular expressions, as not clearly described to be different in contexts, include plural expressions. Terms such as "include" or "have" are for designating presence of features, numbers, steps, operations, elements, components, or combinations thereof mentioned in the specification, and it may be understood as one or more features, numbers, steps, operations, elements, components, or combinations thereof may be further added thereto.

Terms used in the embodiments, as not differently defined, may be understood as meanings generally known to a person skilled in the art. Also, "at least one" may be used as the same meaning as one at a minimum and may selectively designate one or more.

Figure 1A:
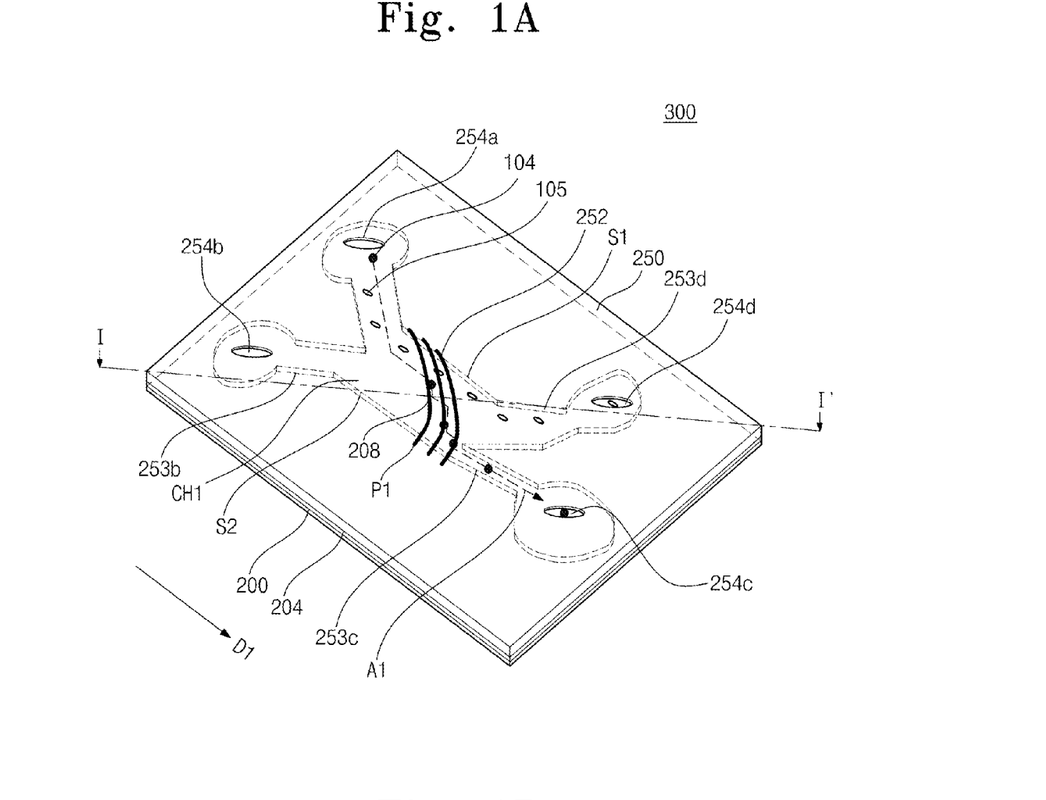
FIG. 1A is a perspective view illustrating a multiple discrimination device according to an embodiment of the present invention.
Figure 1B:
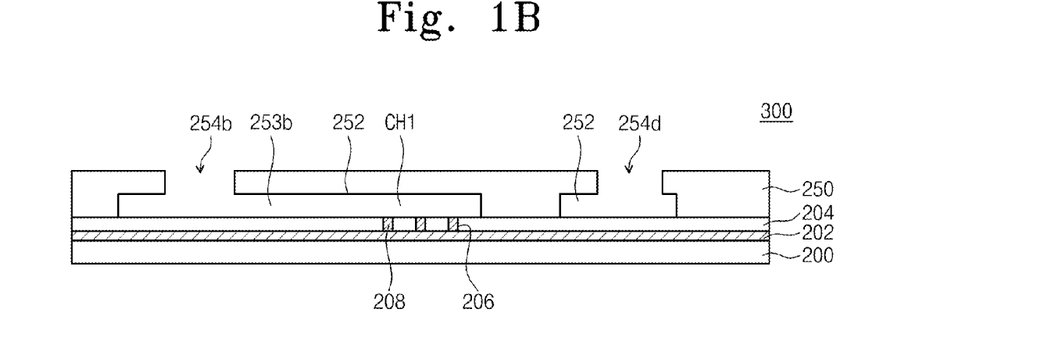
FIG. 1B is a cross-sectional view illustrating a part taken along I-I' shown in FIG. 1A.
Figure 1C:
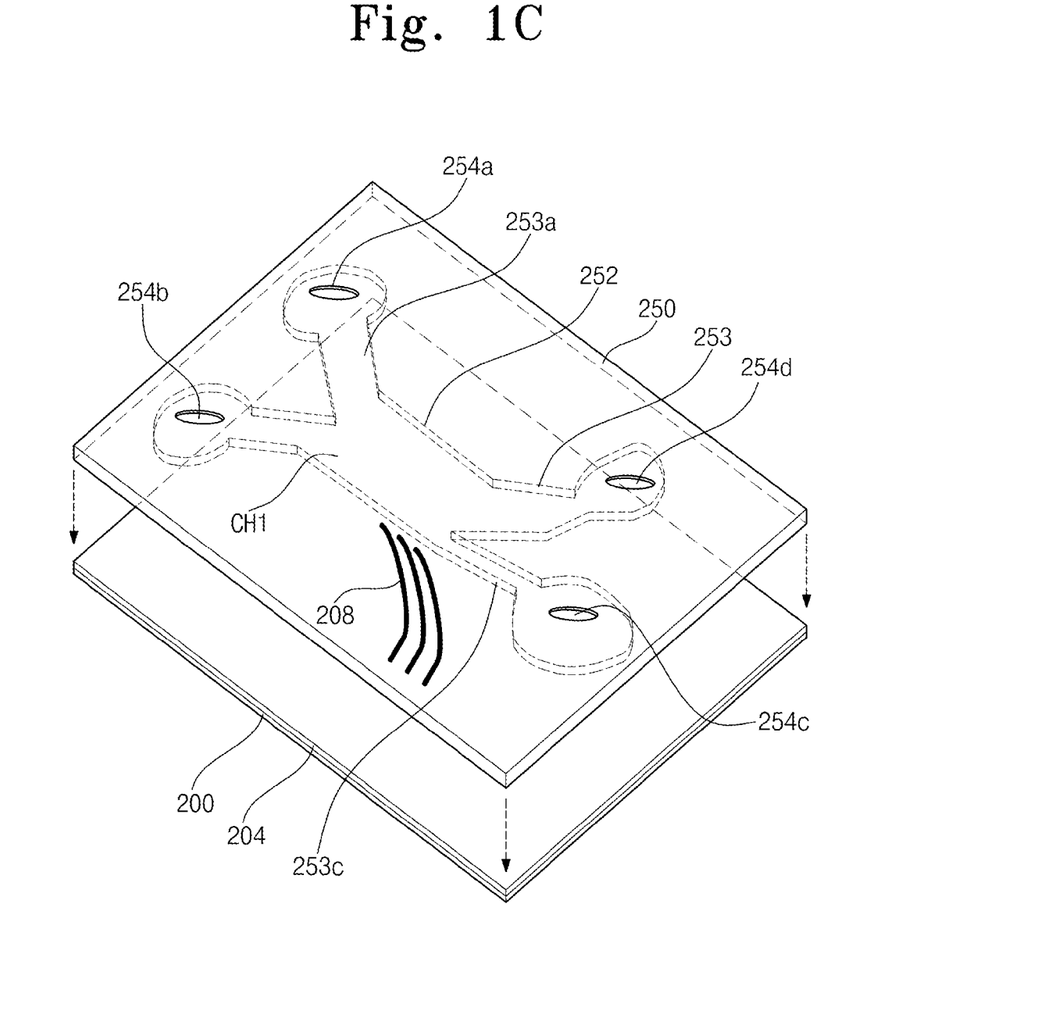
FIG. 1C is an exploded perspective view illustrating the device of FIG. 1.
Figure 2:
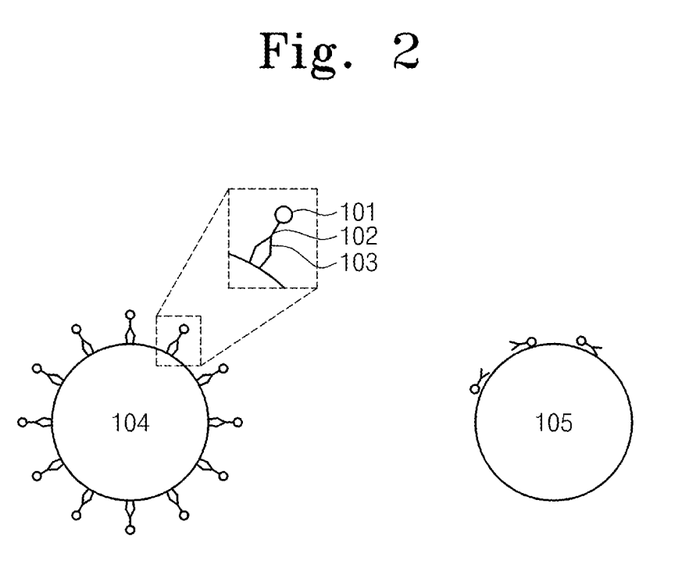
FIG. 2 is a view illustrating species of material included in a mixture solution according to an embodiment of the present invention.
Figure 3A:
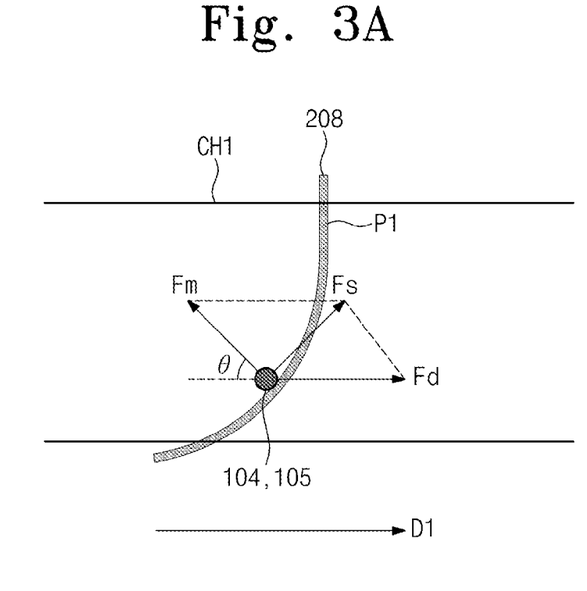
FIG. 3A is a view illustrating a movement of a particle in the multiple discrimination device.
Figure 3B:
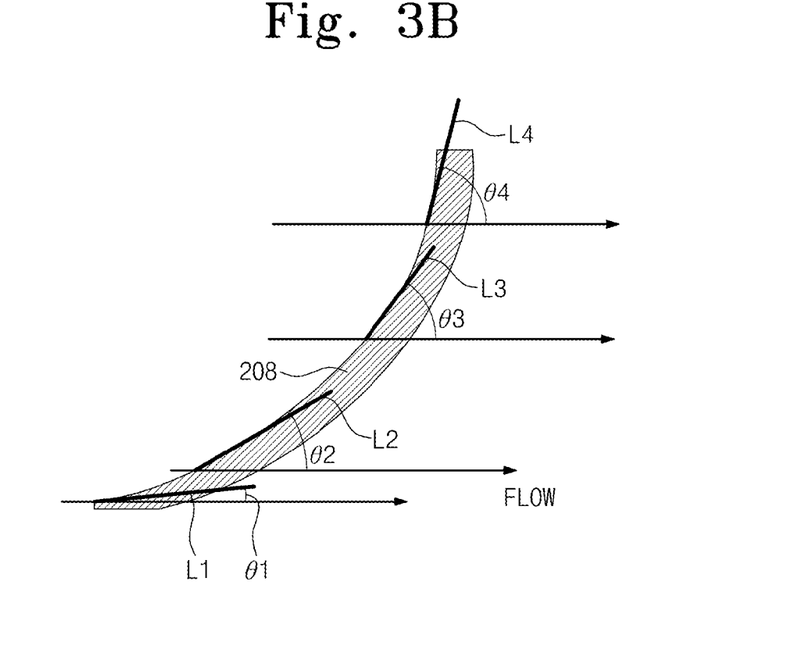
FIG. 3B is an enlarged top view illustrating a ferromagnetic pattern according to an embodiment of the present invention.

FIG. 1A is a perspective view illustrating a multiple discrimination device 300 according to an embodiment of the present invention. FIG. 1B is a cross-sectional view illustrating a part taken along I-I' shown in FIG. 1A. FIG. 1C is an exploded perspective view illustrating the multiple discrimination device 300. FIG. 2 is a view illustrating species of material included in a mixture solution according to an embodiment of the present invention. FIG. 3A is a view illustrating a movement of a particle in the multiple discrimination device 300. FIG. 3B is an enlarged top view illustrating a ferromagnetic pattern 208 according to an embodiment of the present invention.

Referring to FIGS. 1A to 1C, the multiple discrimination device 300 may be formed by bonding a top plate 250 to a bottom plate by using an adhesive or coupling the bottom plate 200 with the top plate 250. A seed layer 200 is disposed on a surface of the bottom plate 202. The seed layer 202 may be formed of at least one film selected from titanium, nickel, and copper or a compound thereof. A bottom photoresist film 204 is disposed on the seed layer 202. The bottom photoresist film 204 is formed with grooves 206 exposing the seed layer 202. Ferromagnetic patterns 208 are disposed in the grooves 206. The ferromagnetic patterns 208 may be formed of a ferromagnetic material, and for example, may include at least one material selected from nickel, nickel-cobalt, nickel-iron, magnesium-aluminum, nickel-iron-copper-chrome, and iron-nickel-molybdenum-magnesium. A thickness of the ferromagnetic pattern 208 may be, for example, from about 0.1 μm to about 1000 μm. Slopes of tangents of the ferromagnetic patterns 208 may continuously vary with a position of the channel CH1. A linear width of the ferromagnetic pattern 208 may be changed according to a location. A width of the ferromagnetic pattern 208 may be from about 10 μm to about 1000 μm. The thickness of the ferromagnetic pattern 208 may be from about 0.1 μm to about 1000 μm.

The top plate 250 includes a hollow recessed part 252 and a plurality of holes 254a to 254d therein. The holes 254a to 254d include a mixture solution inlet 254a into which a mixture solution is inserted, a buffer solution inlet 254b into which a buffer solution such as a saline solution is inserted, a target particle outlet 254c through which a discrimination-target particle 104 is discharged, and an nontarget particle outlet 254d through which a nontarget particle 105 is discharged. The top plate 250 meets the bottom plate 200 and provides a channel CH1 and passages 253a to 253d between the recessed part 252 and a top surface of the bottom plate 200. The passages 253a to 253d include a mixture solution passage 253a connecting the mixture solution inlet 254a to the channel CH1, the buffer solution passage 253b connecting the buffer solution inlet 254b to the channel CH1, a target particle passage 253c connecting the target particle outlet 254c to the channel CH1, and a nontarget particle passage 253d connecting the nontarget particle outlet 254d to the channel CH1. A height of the channel CH1 may be from about 10 μm to about 1000 μm.

At least one of the top plate 250 and the bottom plate 200 may be a polymer substrate formed of at least one selected from cyclo olefin copolymer (COC), polymethylmethacrylate (PMMA), polycarbonate (PC), cyclo olefin polymer (COP), liquid crystalline polymers (LCP), polydimethylsiloxane (PDMS), polyamide (PA), polyethylene (PE), polyimide (PI), polypropylene (PP), polyphenylene ether (PPE), polystyrene (PS), polyoxymethylene (POM), polyetheretherketone (PEEK), polyether sulfone (PES), polyethylenephthalate (PET), polytetrafluoroethylene (PTFE), polyvinylchloride (PVC), polyvinylidene fluoride (PVDF), polybutyleneterephthalate (PBT), fluorinated ethylenepropylene (FEP), and perfluoralkoxyalkane (PFA). Alternatively, at least one of the top plate 250 and the bottom plate may be one of a glass substrate, a silicon substrate, and a metallic substrate. At least one of the top plate 250 and the bottom plate 200 may be formed of one of a PDMS, which is optically transparent and has excellent chemical resistance, and a thermoplastic polymer.

Although not shown in the drawings, to continuously magnetize the ferromagnetic patterns 208, a permanent magnet may be disposed to be adjacent to at least one of the bottom plate 200 and the top plate 250.

The mixture solution flows through the channel CH1 in a first direction D1. Injection, transfer, and discharge of the mixture solution may be flows caused by pressure generated by operations of a syringe pump.

The mixture solution passage 253a and the nontarget particle passage 253d are connected to a first side S1 of the channel CH1, in which the first side S1 may be disposed between the mixture solution passage 253a and the nontarget particle passage 253d. The buffer solution passage 253b and the target particle passage 253d may be connected to a second side S2 of the channel CH1, separated from the first side S1.

As an example, the top plate 250 and the bottom plate 200 may be formed of materials having mutually different hydrophilic property and/or hydrophobic property. Also, films having mutually different hydrophilic property and/or hydrophobic property may be further provided on surfaces of the top plate 250 and the bottom plate 200, which face each other. This is to allow a transfer velocity of a fluid specimen to be controlled by fabricating a microshape of a channel or modifying a surface of the channel.

Referring to FIGS. 1A and 2, a mixture solution is injected into the mixture solution inlet 254a and a buffer solution such as a saline solution is injected into the buffer solution inlet 254b. The mixture solution includes a discrimination-target particle 104 to be discriminated and nontarget particles 105. To couple the discrimination-target particle 104 with magnetic nano particles 101, the mixture solution may be mixed with the magnetic nano particles 101 coupled with antibodies 102. Since antigens 103 exist on a surface of the discrimination-target particle 104, the antigens 103 are coupled with the antibodies 102. Hereby, the antigens 103, the antibodies 102, and the magnetic nano particles 101 may be sequentially coupled with the surface of the discrimination-target particle 104. Since there is no antigen 103 able to react with the antibody 103 on the nontarget particle 105, the magnetic nano particle 101 may not be specifically coupled therewith. For example, the mixture solution may be blood and the discrimination-target particle 104 may be a tumor cell included in the blood. The tumor cell may be one of a circulating tumor cell (CTC) and a disseminated tumor cell (DTC). The antigens 103 may be, for example, epithelial cellular adhesion molecule (EpCAM) markers. The nontarget particles 105 may be normal cells such as white blood cells included in the blood. Alternatively, the discrimination-target particle 104 may be one of a gene, DNA, RNA, protein, peptide. Since the discrimination-target particle 104 is specifically coupled with the magnetic nano particles 101 and the nontarget particle 105 cannot be specifically coupled with the magnetic nano particles 101, a great difference occurs in number of the magnetic nano particles 101. As the number of magnetic nano particles becomes larger, a magnetization amount becomes larger.

Referring to FIGS. 1A and 3A, when solutions are injected into the mixture solution inlet 254a and the buffer solution inlet 254b, respectively, the solutions flow into the channel CH1 through the mixture solution passage 253a and the buffer solution passage 253b, respectively. In this case, a magnetic force Fm may be applied to the discrimination-target particle 104 and the nontarget particles 105 as Equation 1 as follows.

$$\vec{F}_m \approx |\vec{M}_s| \nabla |\vec{B}|$$ Equation (1)

where $F_m$ designates a magnetic force applied to the discrimination-target particle 104 and the nontarget particles 105, $M_s$ designates a saturated magnetization force to be obtained by the discrimination-target particle 104 and the nontarget particles 105 due to the ferromagnetic pattern 208, and $\nabla B$ designates a magnetic field gradient, generated by the form of the ferromagnetic pattern 208. Since the discrimination-target particle 104 includes relatively more magnetic nano particles 101 than the nontarget particle 105, a saturated magnetization force thereof may become relatively greater. Hereby, a magnetic force received by the discrimination-target particle 104 is much greater than that of the nontarget particle 105. Accordingly, the discrimination-target particle 104 may be more easily captured by the ferromagnetic patterns 208.

A force $F_d$ caused by a flow of the mixture solution is applied to the discrimination-target particle 104 and the nontarget particles 105. Accordingly, a resultant force $F_s$ of the magnetic force Fm and the force $F_d$ caused by the flow of the mixture solution become applied to the discrimination-target particle 104 and the nontarget particles 105. The magnetic force Fm may have a negative value, contrary to that of the force $F_d$ caused by the flow of the mixture solution. A condition for capturing the discrimination-target particle 104 and the nontarget particles 105 by the ferromagnetic pattern 208 satisfies Equation 2 as follows.

$$F_m + F_d \cos \theta < 0$$ Equation (2)

where θ designates an angle between a direction of a flow of a mixture solution and a direction of a force received by a magnetic particle due to a magnetic field gradient. As the angle θ becomes larger, a possibility that the discrimination-target particle 104 and the nontarget particles 105 are not captured by the ferromagnetic pattern 208 but pass therethrough becomes greater.

Referring to FIGS. 1A and 3A, the discrimination target particle 104 may be captured by the ferromagnetic pattern 208 while flowing through the channel CH1 and may be transferred along a surface of the ferromagnetic pattern 208. The discrimination-target particle 104 is separated from the surface of the ferromagnetic pattern 208 and flows along the channel CH1 at a first point P1, in which an angle between a tangent and the first direction at one part on the ferromagnetic pattern 208 is from about 80 to about 90 degrees.

Hereby, the ferromagnetic pattern 208 flows along a first arrow A1 and is discharged through the target particle outlet 254c. However, since a magnetic force applied to the nontarget particle 105 is feeble, the nontarget particle 105 is not captured by the surface of the ferromagnetic pattern 208 and is transferred in an initial direction that is the first direction D1 due to laminar flow properties and is discharged through the nontarget particle outlet 254d. As described above, the discrimination-target particle 104 may be effectively discriminated from the nontarget particle 105.

Since the ferromagnetic pattern 208 is disposed more widely than a width of the entire channel CH1, a magnetic particle trap and the like, in which a magnetic field gradient is locally generated and may have an effect on separation, may be prevented. Also, the ferromagnetic pattern 208 may be formed of a curve without an angled part as shown in FIG. 3B. That is, since slope angles θ1, θ2, θ3, and θ4 of tangents L1, L2, L3, and L4 of the ferromagnetic pattern 208 continuously vary with the position of the channel CH1, a trap phenomenon of the discrimination-target particle 104 does not occur at an undesired position. Also, the magnetic field gradient is gradually increased due to the curved shape, thereby increasing efficiency of discrimination. Also, an angle between a tangent of the ferromagnetic pattern 208 and the first direction D1 at the first point P1 is from about 80 to about 90 degrees, and may be about 90 degrees, thereby preventing the trap of the discrimination-target particle 104. The first point P1 may be disposed to be adjacent to a side of the channel CH1 between the buffer solution passage 253b and the target particle passage 253c.

FIGS. 4A to 4E are schematic top views illustrating exemplary embodiments of the present invention.

Figure 4A:
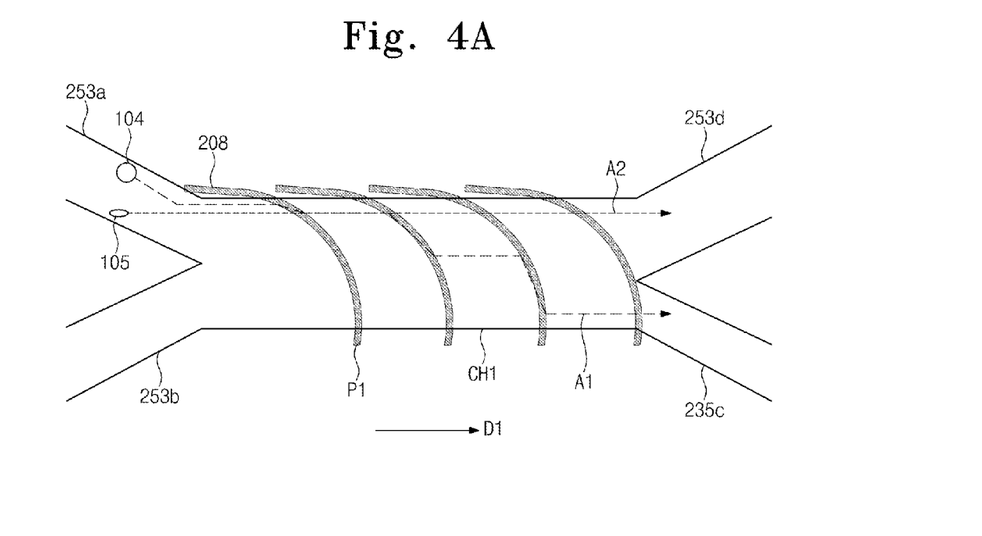
FIGS. 4A to 4E are schematic top views illustrating exemplary embodiments of the present invention.
Figure 4B:
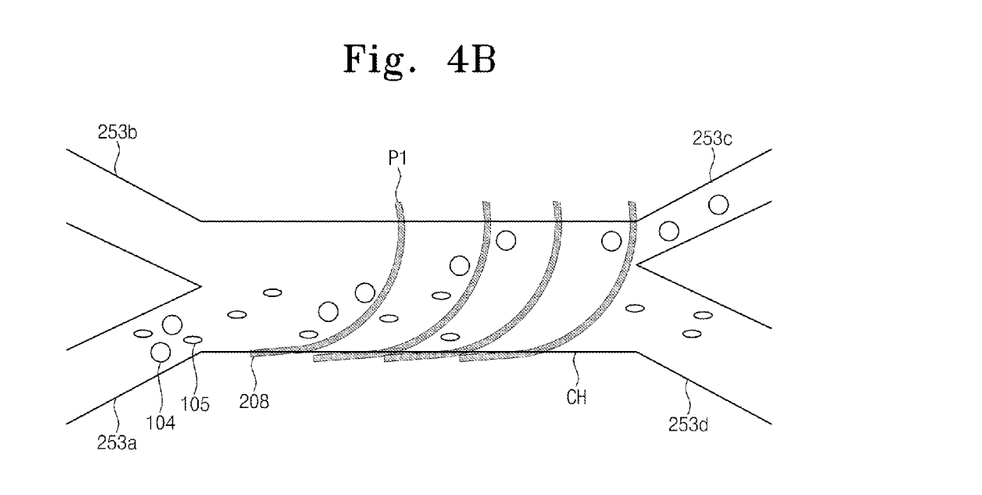

Referring to FIG. 4A, the number of the ferromagnetic pattern 208 may be plural and an interval between the ferromagnetic patterns 208 may become wider as closer to the target particle outlet 253c and the nontarget particle outlet 253d. Alternatively, referring to FIG. 4B, the interval between the ferromagnetic patterns 208 may become narrower as closer to the target particle outlet 253c and the nontarget particle outlet 253d. In FIGS. 1A, 1C, 3, 4A, and 4B, planar shapes of the all ferromagnetic patterns 208 may be similar to the shape of "J". In this case, the first point P1 may be disposed to be adjacent to the side of the channel CH1 between the buffer solution passage 253b and the target particle passage 253c.

Figure 4C:
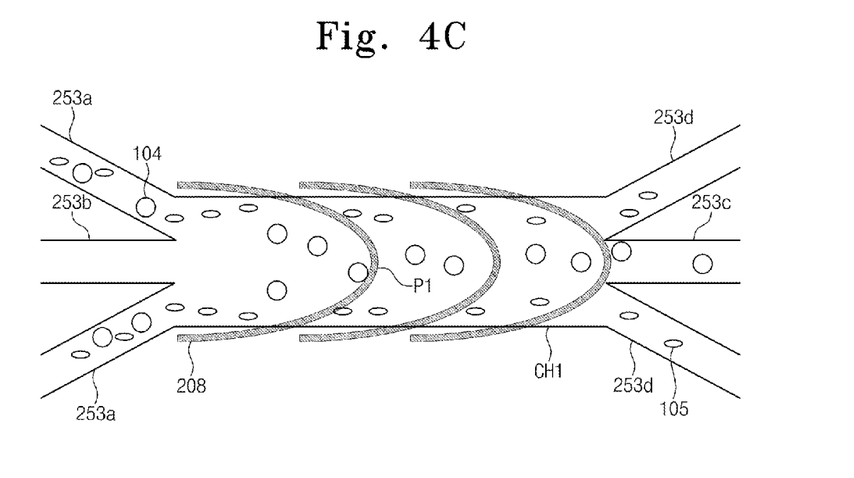
Figure 4D:
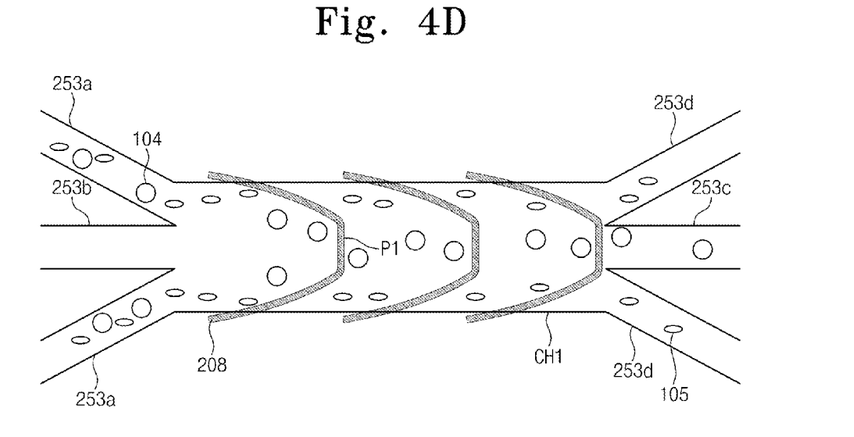

Alternatively, referring to FIGS. 4C and 4D, the planar shapes of the ferromagnetic patterns 208 may be similar to the shape of "U". Also, two mixture solution passages 253a and two nontarget particle passages 253d may be included. Alternatively, referring to FIG. 4E, the planar shapes of the ferromagnetic patterns 208 may be similar to the shape of "ω".

Figure 4E:
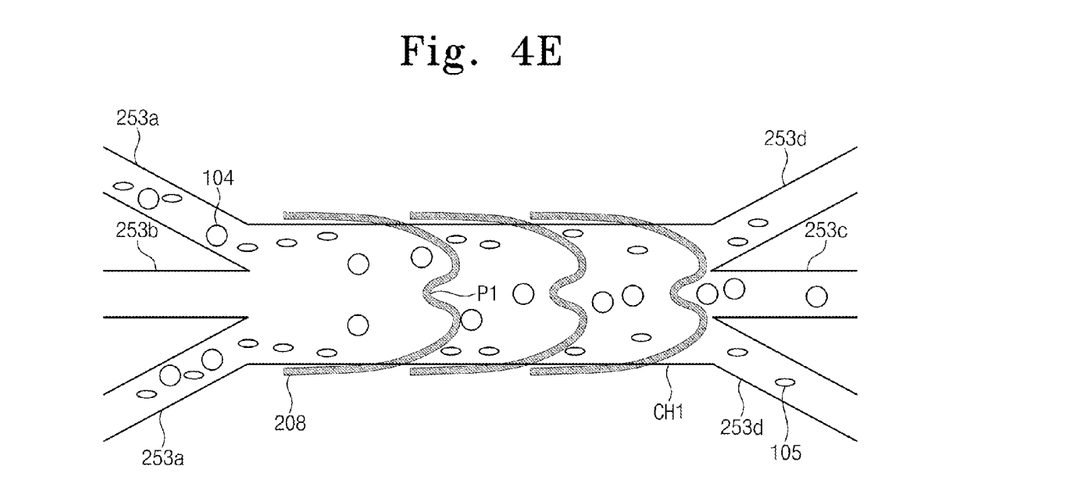

In FIGS. 4C, 4D, and 4E, particle discrimination may be performed in the center of the channel CH1. As shown in FIGS. 1A, 1C, 3, 4A, and 4B, when the particle discrimination occurs at the first point P1 adjacent to the side of the channel CH1, an eddy that may occur in a wall of the channel CH1 may have a bad effect on the particle discrimination. However, as shown in FIGS. 4C, 4D, and 4E, when discrimination occurs in the center of the channel CH1, the bad effect caused by the eddy may be excluded.

When the mixture solution is blood containing tumor cells, for example, the blood contains one billion cells per one milliliter, in which most thereof may be normal cells and tumor cells may be from about several to about several tens. The type of cancer and whether the cancer is ongoing or not may be checked by using the kind and number of captured tumor cells. Accordingly, it is necessary that the most discrimination-target particles 104 go through the target particle passage 253c, that is, the discrimination-target particles 104 are well captured.

A primary factor having an effect on the capture of the discrimination-target particles 104 is a planar pattern shape of the ferromagnetic pattern 208. When the ferromagnetic pattern 208 has a shape of a broken line having a discontinuously varying slope instead of a curved line having a continuously varying slope, the discrimination-target particles 104 may be trapped at a part in which the line is broken. As described above, when the discrimination-target particle 104 is trapped at an involuntary position, efficiency of discrimination will be decreased. Accordingly, in FIGS. 4A to 4E, the planar shapes of the ferromagnetic patterns 208 have curved shapes with continuously varying tangent slopes to increase the efficiency of discrimination.

A secondary factor having an effect on the capture of the discrimination-target particle 104 is a side wall or an interface of the channel CH1. A flow velocity is highest at the center of the channel CH1 and is lowest at the side wall or the interface of the channel CH1 (Theoretically, the flow velocity is almost zero at the side wall or the interface of the channel CH1). Also, when the ferromagnetic pattern 208 is disposed on the side wall or the interface, the discrimination-target particles 104 may be trapped so not to flow therethrough. Also, an eddy of a fluid that is the mixture solution occurs around the side wall or the interface of the channel CH1 or an air bubble occurs at the sidewall of the interface. This eddy or the air bubble may have a bad effect on the discrimination of particles. As shown in FIGS. 4C, 4D, and 4E, when the ferromagnetic patterns 208 have shapes of U and ω, discrimination is performed in the center of the channel CH1, thereby overcoming such limitations.

A third factor having an effect on the capture of the discrimination-target particles 104 is reducing that the discrimination-target particles 104 go through the nontarget particle passage 253c that is involuntary, at an outlet side. When the mixture solution, for example, blood and the buffer solution having different densities from each other flow in through the inlets 254a and 254b, a fluid moves toward a part having low density at the same flow velocity. That is, the mixture solution forces its way through toward the buffer solution. Then only the discrimination-target particles 104 are captured from the mixture solution and the nontarget particles 105 are allowed to go through the nontarget particle passage 254d by controlling the flow velocity. Also, in a micro channel, most flows are laminar flows but a width of the channel CH1 varies at the passages 253a and 254d, thereby generating an eddy. Due to this eddy, some of the discrimination-target particles 104 may go through the nontarget particle passage 253c. A structure for preventing the discrimination-target particles 10 from going through the nontarget particle passage 253c is necessary. When the ferromagnetic pattern 208 has the shape of ω as shown in FIG. 4E, a magnetic force that the discrimination-target particle 104 receives is reduced according to Equations 1 and 2 in such a way that almost only a force according to the laminar flow of the fluid has an effect on discriminated discrimination-target particles 104. According thereto, a state in which the discriminated discrimination-target particles 104 are separated according to the laminar flow is well maintained, thereby capturing the discrimination-target particles 104 without loss to capacity.

Hereinafter, a process of manufacturing the multiple discrimination device will be described.

The top plate 250 and the bottom plate 200 of the multiple discrimination device may be formed by using one selected from typical mechanic processing methods such as injection molding, hot embossing, casting, stereolithography, laser ablation, rapid prototyping, silk screen, numerical control (NC) machining and a semiconductor processing method using photolithography, respectively. It is preferable to use a photolithography process.

Microstructures as described above are formed on the top plate 250 and the bottom plate 200, and then the top plate 250 and the bottom plate 200 are coupled with each other. In this case, a functional material for surficial adhesion is formed by using surface modification such as surface plasma processing and self-assembled film forming processes and coupled by using thermal treatment while applying pressure thereto. Alternatively, a top plate and a bottom plate may be coupled with each other by using an adhesive. When the top plate 250 and the bottom plate 200 are formed of same material, an adhesive element may be heat, chemicals, or ultrasonic waves. When the top plate 250 and the bottom plate 200 are formed of different materials, the adhesive element may be a liquid adhesive material, a powder adhesive material, and an adhesive material having a thin panel shape such as paper. While coupling the top plate 250 with the bottom plate 200, a pressure sensitive adhesive material forming adhesion only by using pressure may be used when room temperature or a low temperature adhesion is necessary to prevent denaturalization of a biochemical material such as antibodies.

As a detailed example, a process of forming a bottom plate will be described with reference to FIGS. 5A to 5E.

Referring to FIG. 5, the bottom plate 200 is prepared. The bottom plate 200 may be, for example, a silicon wafer, and may be cleaned.

Figure 5A:
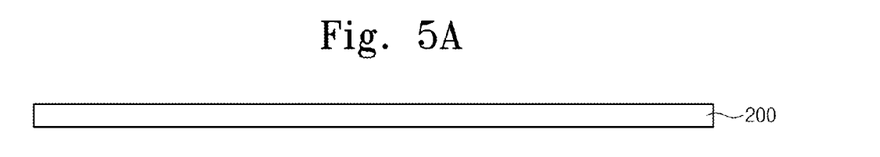
FIGS. 5A to 5E are views illustrating a method of manufacturing a bottom plate of FIG. 1B.
Figure 5B:
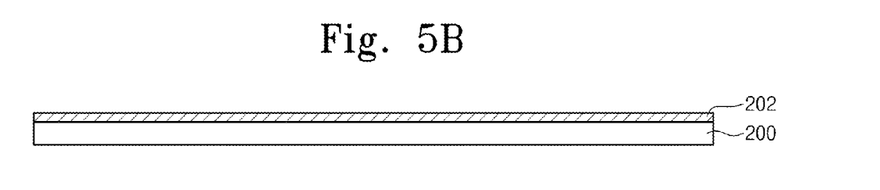

Referring to FIG. 5B, the seed layer 202 is formed on a top of the bottom plate 200. The seed layer 202 may be formed of at least one film selected from titanium, nickel, and copper or a compound thereof through a deposition process.

Figure 5C:
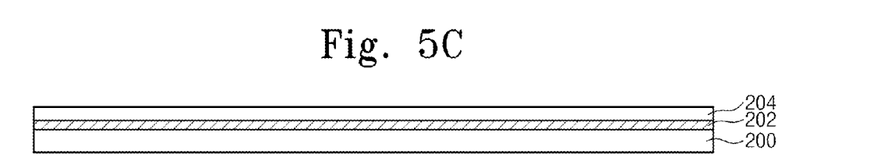

Referring to FIG. 5C, the bottom photoresist film 204 is formed on the seed layer 202.

Figure 5D:
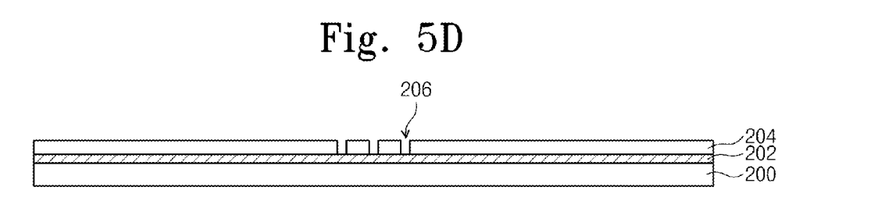

Referring to FIG. 5D, a plurality of grooves 206 exposing the seed layer 202 is formed on the bottom photoresist film 204 through light exposure and developing processes.

Figure 5E:
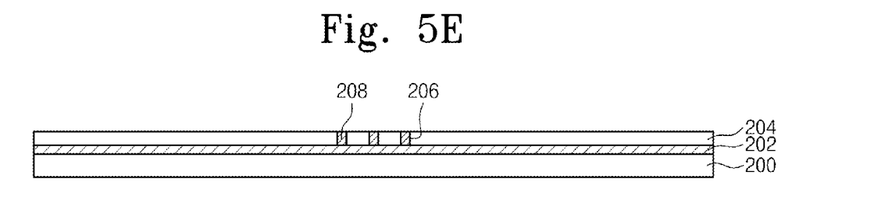

Referring to FIG. 5E, the ferromagnetic patterns 208 filling the grooves 206 are formed by using one of an electroplating method and a deposition process using electron beams. The ferromagnetic patterns 208 may be formed of at least one material selected from nickel, nickel-cobalt, nickel-iron, magnesium-aluminum, nickel-iron-copper-chrome, and iron-nickel-molybdenum-magnesium. In this case, a thickness of the ferromagnetic pattern 208 may be, for example, from about 0.1 μm to about 1000 μm. As a follow-up, a planarization process such as chemical-mechanical polishing may be performed to planarize a surface. Hereby, the bottom plate 200 may be formed.

A process of manufacturing the top plate 250 will be described with reference to FIG. 6A to 6D.

Figure 6A:
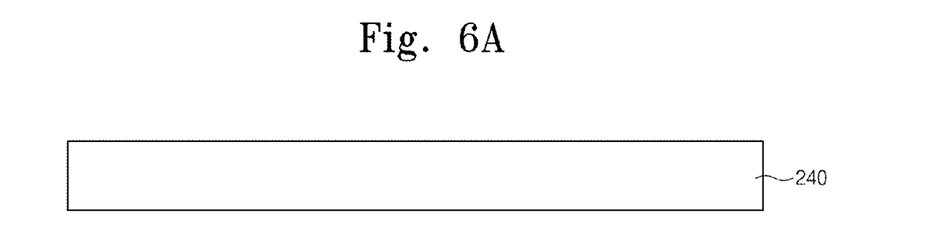

Referring to FIG. 6A, a mold substrate 240 is formed. The mold substrate 240 may be, for example, a silicon wafer.

Referring to FIG. 6B, a top photoresist pattern 242 is formed on the mold substrate 240. To form the top photoresist pattern 242, an epoxy series of photosensitive photoresist may be applied. A thickness of the photoresist may be variously controlled by controlling a coefficient of viscosity of the photoresist or in proportion to an rpm, for example, from about 500 to about 5000 rpm such as from about 1 μm to about 1000 μm. The epoxy series of photosensitive photoresist may form an accurate pattern without an effect although a light exposure process is additionally performed after a thermal cure and may easily and quickly obtain desired pattern and depth by the light exposure process. As an example, the epoxy series of photoresist may be an SU-8 series of negative photoresist. An accurate pattern shape such as resolution of 1 μm or more may be controlled by a pattern of a light exposure mask. Through the process, an original top plate mold including the top photoresist pattern 242 corresponding to a fluid channel shape having micro channel depth and pattern shape may be completed.

Figure 6C:
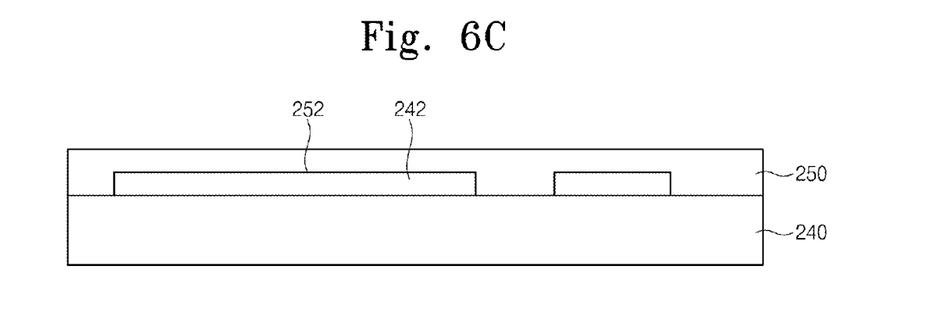

Referring to FIG. 6C, the top plate 250 is formed by coating the mold substrate 240 with a PDMS material and curing the same.

Figure 6D:
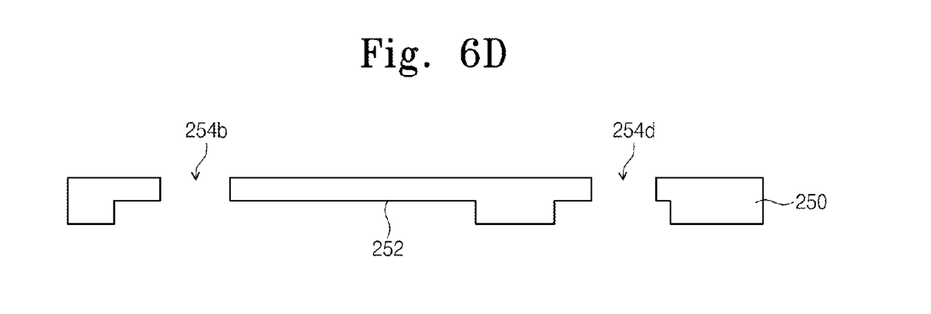

Referring to FIG. 6D, the top plate 250 is separated from the mold substrate 240. The recessed part 252 may be formed on the top plate 250, where the top photoresist pattern 242 existed. Also, the holes 254a to 254d may be formed by punching.

Although not shown in the drawings, before coating with the PDMS material, a structure of the original top plate mold is electroplated, thereby manufacturing a metallic mold. The electroplating may be performed after forming a seed layer formed of a metal such as Ti, Cr, Al, Au, and the like. A thickness of the metallic mold may not be bent or broken while being transferred to a substrate, for example, a polymer substrate. After that, the mold substrate, for example, a silicon substrate is removed by using a wet etching method and the like to allow only the metallic mold to remain.

The metallic mold may be transferred to a substrate, for example, a polymer substrate by using one of an injection molding method, a hot embossing method, a casting method, and the like. After that, the holes 254a to 254d may be formed.

Referring to FIG. 1C, the top plate 250 is coupled to the bottom plate 200. In this case, the ferromagnetic pattern 208 is coupled with the channel CH1 to correspond to each other. When being formed of same material, the top plate 250 and the bottom plate 200 may be adhered to each other by using heat, chemicals, or ultrasonic waves. When being formed of different materials, the top plate 250 and the bottom plate 200 may be adhered to each other by using a liquid adhesive material, a powder adhesive material, and an adhesive material having a thin panel shape such as paper. While coupling the top plate 250 with the bottom plate 200, a pressure sensitive adhesive material forming adhesion only by using pressure may be used when room temperature or a low temperature adhesion is necessary to prevent denaturalization of a biochemical material such as antibodies.

According to the multiple discrimination device according to present embodiment, three-dimensional micro ferromagnetic patterns are optimally designed and arranged in such a way that a magnetic force applied to a discrimination-target particle to be discriminated may be well controlled to perform discrimination well. The ferromagnetic patterns are disposed on a bottom of a channel to allow a transfer of bio particles to be easily controlled, thereby selectively discriminating only the discrimination-target particle.

Also, a slope of a tangent of the ferromagnetic patterns continuously varies with a position of the channel, thereby well discriminating target particles without loss caused by a trap of the target particle at an involuntary position.

The method of manufacturing the multiple discrimination device uses a semiconductor processing technology, thereby precisely manufacturing the devices and allowing mass production.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A multiple discrimination device comprising:
    a top plate;
    a bottom plate;
    a seed layer disposed between the top plate and the bottom plate; and
    at least one ferromagnetic pattern disposed between the top plate and the seed layer, the at least one ferromagnetic pattern being adjacent to the seed layer,
    wherein the top plate comprises:
    a channel parallel with a first direction and having a first end and a second end, a mixture solution flowing from the first end to the second end;
    at least one mixture solution inlet connected to the first end of the channel;
    a buffer solution inlet connected to the first end of the channel;
    a target particle outlet through which the discrimination target particle is discharged, the target particle outlet being connected to the second end of the channel; and
    a nontarget particle outlet through which the nontarget particle is discharged, the nontarget particle outlet being connected to the second end of the channel,
    wherein each of the at least one ferromagnetic pattern continuously curves underneath the entire channel and extends underneath both sides of the channel, and
    wherein the mixture solution comprises a discrimination-target particle and a nontarget particle.

2. The device of claim 1, wherein each of the at least one ferromagnetic pattern has at least one shape of 'J', 'U', and 'ω'.

3. The device of claim 1, wherein a width of each of the at least one ferromagnetic pattern varies.

4. The device of claim 1, wherein a width of each of the at least one ferromagnetic pattern is between about 10 μm to about 1000 μm.

5. The device of claim 1, wherein a thickness of each of the at least one ferromagnetic pattern is between about 0.1 μm to about 1000 μm.

6. The device of claim 1, wherein a height of the channel is between about 10 μm to about 1000 μm.

7. The device of claim 1, further comprising at least one permanent magnet disposed adjacent to the channel.

8. The device of claim 1, wherein the at least one ferromagnetic pattern is a plurality of ferromagnetic patterns, and wherein intervals between the plurality of ferromagnetic patterns become narrower towards the nontarget particle outlet.

9. The device of claim 1, wherein a magnetization amount of the discrimination-target particle is larger than that of the nontarget particle.

10. The device of claim 9, wherein the discrimination-target particle is coupled with a magnetic nano particle and is at least one of a gene, DNA, RNA, protein, peptide, and a tumor cell.

11. The device of claim 1,
    wherein the at least one ferromagnetic pattern is disposed on the bottom plate,
    wherein the top plate is disposed above the bottom plate, and
    wherein at least one of the bottom plate and the top plate comprises polydimethylsiloxane (PDMS).

12. The device of claim 11, further comprising a photoresist pattern disposed between the bottom plate and the top plate and being in contact with a sidewall of each of the at least one ferromagnetic pattern.

13. The device of claim 1, wherein each of the at least one ferromagnetic pattern has a 'ω' shape.

14. The device of claim 1, wherein a magnetic field gradient produced by the plurality of ferromagnetic patterns increases along the first direction.

15. A multiple discrimination device comprising:
    a top plate;
    a bottom plate;
    a seed layer disposed between the top plate and the bottom plate; and
    a plurality of ferromagnetic patterns disposed between the top plate and the seed layer,
    wherein the top plate comprises:
    a channel parallel with a first direction and having a first end and a second end, a mixture solution flowing from the first end to the second end;
    at least one mixture solution inlet connected to the first end of the channel;
    a buffer solution inlet connected to the first end of the channel;
    a target particle outlet through which the discrimination target particle is discharged, the target particle outlet being connected to the second end of the channel; and
    a nontarget particle outlet through which the nontarget particle is discharged, the nontarget particle outlet being connected to the second end of the channel, and
    wherein each of the plurality of ferromagnetic patterns continuously curves underneath the entire channel and extends underneath both sides of the channel, each of the ferromagnetic patterns being wider than a width of the channel.

16. The device of claim 15, wherein intervals between the plurality of ferromagnetic patterns become narrower towards the nontarget particle outlet.

* * * * *